United States Patent [19]

Takaya et al.

[11] Patent Number: 4,554,269

[45] Date of Patent: Nov. 19, 1985

[54] KASUGAMYCIN DERIVATIVES, PHARMACEUTICAL COMPOSITIONS AND METHOD OF USE

[75] Inventors: Takao Takaya, Kawanishi; Nobuyoshi Yasuda, Nishinomiya; Hideo Tsutsumi, Toyonaka; Keiji Matsuda, Takatsuki, all of Japan

[73] Assignee: Fujisawa Pharmaceutical Co., Ltd., Osaka, Japan

[21] Appl. No.: 573,377

[22] Filed: Jan. 24, 1984

[30] Foreign Application Priority Data

Jan. 28, 1983 [GB] United Kingdom ................ 8302439
Jun. 20, 1983 [GB] United Kingdom ................ 8316699

[51] Int. Cl.$^4$ ...................... A61K 31/71; C07H 15/20
[52] U.S. Cl. ...................................... 514/35; 536/16.7
[58] Field of Search ............................ 536/16.7, 16.8; 424/180; 514/35

[56] References Cited

U.S. PATENT DOCUMENTS

| | | | |
|---|---|---|---|
| 3,244,590 | 4/1966 | Schaffner et al. | 536/16.8 |
| 3,647,779 | 3/1972 | Schmitz | 536/16.7 |
| 3,652,535 | 3/1972 | Keil et al. | 536/16.7 |
| 4,044,123 | 8/1977 | Daniels et al. | 536/16.8 |
| 4,468,512 | 8/1984 | Kirst et al. | 536/16.8 |

*Primary Examiner*—Johnnie R. Brown
*Attorney, Agent, or Firm*—Oblon, Fisher, Spivak, McClelland & Maier

[57] ABSTRACT

This invention relates to new aminoglycoside derivatives and pharmaceutically acceptable salts thereof. More particularly it relates to new aminoglycoside derivatives and pharmaceutically acceptable salts thereof which have anti-viral activity, and immuno-stimulating activity and pharmaceutical compositions comprising the same. In addition, this invention also relates to methods of preparing the aminoglycoside derivatives and salts thereof.

13 Claims, No Drawings

KASUGAMYCIN DERIVATIVES, PHARMACEUTICAL COMPOSITIONS AND METHOD OF USE

BACKGROUND OF THE INVENTION

Field of the Invention

This invention relates to new aminoglycoside derivatives and pharmaceutically acceptable salts thereof. More particularly, it relates to new aminoglycoside derivatives and pharmaceutically acceptable salts thereof which have antiviral activity, and immunostimulating activity, processes for the preparation thereof and a pharmaceutical composition comprising the same.

SUMMARY OF THE INVENTION

Accordingly, it is an object of this invention to provide new aminoglycoside derivatives which are useful as prophylactic and therapeutic agents for infectious diseases caused by pathogenic microorganisms.

Another object of this invention is to provide processes for preparing the aminoglycoside derivatives.

Further object of this invention is to provide a pharmaceutical composition comprising the aminoglycoside derivatives.

Having now briefly described the invention, a more complete understanding of the invention can be obtained by reference to the description of the preferred embodiments which is provided herein for purposes of illustration only, and is not intended to be limiting unless otherwise specified.

DESCRIPTION OF THE PREFERRED EMBODIMENTS

The new aminoglycoside derivatives of this invention can be represented by the following formula:

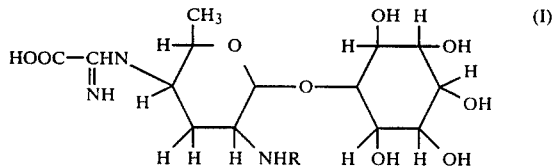

(I)

wherein R is acyl.

According to this invention, the new aminoglycoside derivatives (I) can be prepared by, for example, the following processes.

Process 1

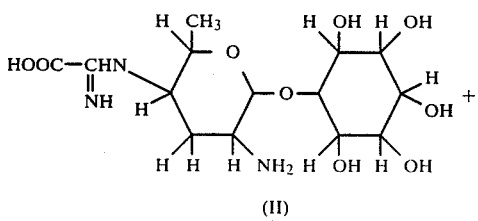

(II)

or its reactive derivative at the amino group or a salt thereof

-continued

ROH ⟶ (III)

or its reactive derivative at the carboxy group or a salt thereof

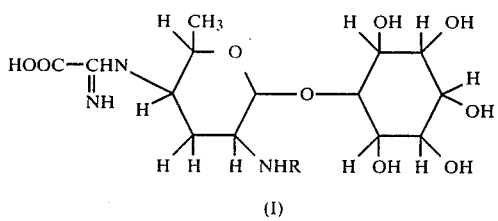

(I)

or a salt thereof

Process 2

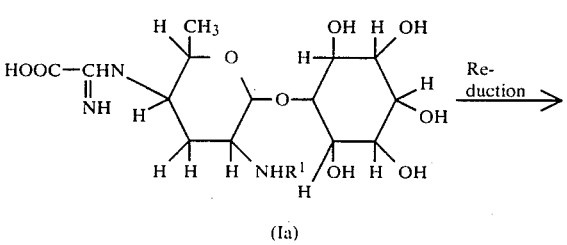

(Ia)

or a salt thereof

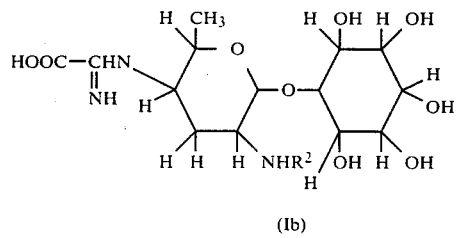

(Ib)

or a salt thereof wherein
R is as defined above,
$R^1$ is higher alkenoyl, and
$R^2$ is higher alkanoyl.

Suitable pharmaceutically acceptable salts of aminoglycoside derivatives (I), (Ia), (Ib) and salt of the starting compound (II) are conventional salts and may include an organic or inorganic acid addition salt such as hydrochloride, hydrobromide, hydriodide, sulfate, nitrate, carbonate, phosphate, acetate, fumarate, maleate, tartrate, methanesulfonate, benzenesulfonate, toluenesulfonate, and the like.

In the above and subsequent descriptions of this specification, suitable examples and illustrations of the various definitions are explained in detail in the following.

The term "lower" is intended to mean 1 to 6 carbon atom(s), unless otherwise provided.

"Acyl" may include aliphatic acyl group and acyl group containing an aromatic or heterocyclic ring. And, suitable examples of the acid acyl may be lower alkanoyl (e.g. formyl, acetyl, propionyl, butyryl, isobutyryl, valeryl, isovaleryl, oxalyl, succinyl, pivaloyl, hexanoyl, etc.); higher alkanoyl (e.g. octanoyl, decanoyl, lauroyl, myristoyl, pentadecanoyl, palmitoyl, heptadecanoyl, stearoyl, icosanoyl, docosanoyl, etc.) having 7 to 24 carbon atoms; higher alkenoyl (e.g. octenoyl, decenoyl, icosenoyl, docosenoyl, etc.) having 7 to 24 carbon atoms; or the like. The acyl is stated above may have at least one suitable substituent(s) such as halogen (chlorine, bromine, fluorine and iodine), hydroxy or amino, or the like. Preferred embodiments of the object compound (I) are as follows. Preferred embodiment of R is higher alkanoyl or higher alkenoyl.

The processes for preparing the object compounds of the present invention are explained in detail in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include silyl derivative formed by the reaction of the compound (II) with a silyl compound such as bis(trimethylsilyl)acetamide, mono(trimethylsilyl)acetamide or the like; and the like.

Suitable salt of the compounds (II) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.) and the like.

Suitable salt of the compounds (III) may include a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction can preferably be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

When the acylating agent is used in a form of free acid, the reaction of this process may preferably be conducted in the presence of a condensing agent such as carbodiimidic compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonyldiimidazole, N,N-carbonyldi(2-methylimidazole), pentamethyleneketene-N-cyclohexylimine, diphenylketene-N-cyclohexylimine, alkoxyacetylene, 1-alkoxy-1-chloroethylene, trialkylphosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, N-ethyl-5-phenylisoxazolium-3'-sulfonate, 2,2,4,4,6,6-hexachloro-1,3,5,2,4,6-triazatriphosphorine, 1-benzenesulphonyloxy-6-chloro-1H-benzotriazole, p-toluenesulfonyl chloride, isopropoxybenzenesulfonyl chloride, or a mixed condensing agent such as triphenylphosphine and a carbon tetrahalide (e.g. carbon tetrachloride, carbon tetrabromide, etc.) or so-called Vilsmeier reagent (e.g. a complex of N,N-dimethylformamide with phosphoryl chloride, phosgene of thionyl chloride.

The reaction is usually conducted in a conventional solvent which does not adversely influence the reaction such as water, acetone, dioxane, acetonitrile, ethyl acetate, N,N-dimethylformamide, dimethylsulfoxide, tetrahydrofuran, dichloromethane, chloroform, pyridine, N-methylmorpholine, N-methylpyrrolidine, etc. or a mixture thereof.

The reaction temperature is not critical and this reaction can be conducted within the temperature range of cooling to heating.

PROCESS 2

The object compound (Ib) or a salt thereof can be prepared by reducing the compound (Ia) or a salt thereof.

Suitable reduction may include, for example, catalytic reduction or the like. Suitable catalyst includes a conventional one, for example, Raney nickel, platinum oxide, palladium carbon and the like.

The present reduction is usually carried out in a solvent such as water, acetone, dioxane, acetonitrile, dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

The object compound (I) and pharmaceutically acceptable salts thereof have antiviral activity and immuno-stimulating activity and therefore, are useful as an antiviral agent for human beings, animals and plants and a prophylactic agent for infectious diseases caused by pathogenic microorganisms.

For prophylactic or therapeutic administration, the object compound (I) and the pharmaceutically acceptable salts thereof of the present invention are used in the form of conventional pahrmaceutical preparation comprising the same, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule or liquid form such as solution, suspension, syrup, emulsion, lemonade and the like. If needed, there may be included in the above preparations auxiliary substances, stabilizing agents, wetting agents and other commonly used additives such as lactose, magnesium stearate, terra alba, sucrose, corn starch, talc, stearic acid, gelatin, agar, pectin, peanut oil, olive oil, cacao butter, ethylene glycol and the like.

While the dosage of the compound (I) or pharmaceutically acceptable salts thereof may vary from and also depend upon the age, conditions of the patient, kinds of diseases, kinds of the compound (I) or pharmaceutically acceptable salts thereof to be applied, etc. In general, preferable dosage of the compound (I) or pharmaceutically acceptable salts thereof to the patient can be selected from 0.1–100 mg/kg/day.

The following Preparation and Examples are given for the only purpose of illustrating this invention and are not intended to be limiting unless otherwise specified. These examples will provide a more complete understanding of the invention, which heretofore has been described generally. In the Examples, it is to be noted that the numbering of the carbon atom's positions of the aminoglycoside derivatives is given in accordance with that of Kasugamycin as illustrated in the following diagram.

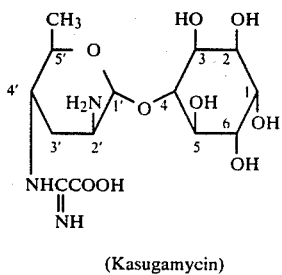

(Kasugamycin)

In order to illustrate the usefulness of the object compound, the anti-viral activity of a representative compound of the present invention is shown below.

EXAMPLES

The assays were carried out in confluent Vero cell cultures in multi-well trays (96 wells). For these experiments, cell cultures were grown to confluence in Eagle's minimal essential medium (MEM) supplemented with 5% fetal bovine serum (FBS).

Anti-HSV (herpes simplex virus) activity (A) Test Method

The cuture medium was changed to 0.5% FBS-MEM. The cell cultures were inoculated with about 100 $TCID_{50}$ of HSV-I Miyama strain, and immediately thereafter, exposed to varying concentrations of the test compound and incubated for 2 days at 37° C. in humidified 5% $CO_2$-95% air. 4 wells were used in each concentrations. They were fixed with 5% trichloroacetic acid and stained with 0.1% crystalviolet. The viral CPE was observed microscopically (x40). Antiviral activity was expressed as $ID_{50}$ (50% inhibitory dose), that is, the concentration of compound required to reduce viral CPE by 50% (within the well), when it had reached completion (100% cell destruction) in the control virus-infected cell cultures.

(B) Test Compound
2'-N-palmitoylkasugamycin (C) Test Result

| Anti-HSV activity (μg/ml) |
|---|
| 3.2 |

Preparation 1

A solution of decanoyl chloride (5.0 g) in tetrahydrofuran (20 ml) was dropwise added to a mixture of N-hydroxysuccinimide (3.06 g) and triethylamine (3.7 ml) in tetrahydrofuran (30 ml) with stirring under ice-cooling. The mixture was stirred at the same temperature for one hour and then at ambient temperature for 15 hours. A precipitate was filtered off and the filtrate was concentrated under reduced pressure. The residue was dissolved in ethyl acetate (50 ml). The solution was washed with water (50 ml), dried over magnesium sulfate, and concentrated under reduced pressure. The residue was crystallized from ethyl acetate-hexane to give N-decanoyloxysuccinimide as a crystal (4.95 g).

mp: 70°–71° C.

IR (Nujol): 1825, 1790, 1730 cm$^{-1}$

NMR (CDCl$_3$, δ): 0.87 (3H, t, J=4.5 Hz), 2.58 (2H, t, J=7 Hz), 2.94 (4H, s)

Preparation 2

The following compounds were obtained in a similar manner to that of Preparation 1.

(1) N-Lauroyloxysuccinimide mp: 76°–77° C.

IR (Nujol): 1825, 1790, 1730 cm$^{-1}$

NMR (CDCl$_3$, δ): 0.89 (3H, t, J=4.5 Hz), 2.59 (2H, t, J=7 Hz), 2.80 (4H, s)

(2) N-Myristoyloxysuccinimide mp: 83°–84° C.

IR (Nujol): 1820, 1790, 1740, 1730 cm$^{-1}$

NMR (CDCl$_3$, δ): 0.90 (3H, t, J=5 Hz), 2.60 (2H, t, J=7 Hz), 2.83 (4H, s)

(3) N-Pentadecanoyloxysuccinimide mp: 60°–63° C.

IR (Nujol): 1820, 1790, 1740, 1730 cm$^{-1}$

NMR (CDCl$_3$, δ): 0.90 (3H, t, J=5 Hz), 2.60 (2H, t, J=7 Hz), 2.83 (4H, s)

(4) N-Stearoyloxysuccinimide

IR (Nujol): 1820, 1790, 1740, 1730 cm$^{-1}$

NMR (CDCl$_3$, δ): 0.87 (3H, t, J=5 Hz), 2.60 (2H, t, J=7 Hz), 2.80 (4H, s)

(5) N-Palmitoyloxysuccinimide

IR (Nujol): 1820, 1780, 1720 cm$^{-1}$

EXAMPLE 1

To a suspension of Kasugamycin Hemisulfate (428 mg) in a mixture of tetrahydrofuran (20 ml) and water (20 ml) was added sodium hydrogen carbonate (92 mg) and N-palmitoyloxysuccinimide (389 mg). The mixture was stirred at ambient temperature overnight and then refluxed for 4 hours. Tetrahydrofuran was removed from the mixture by distillation at 1 atm. The aqueous mixture was adjusted to pH 2 with 1N-hydrochloric acid. The insoluble material was filtered and washed with water. The filtrate and washings were combined, adjusted to pH 6.85 with saturated aqueous sodium hydrogen carbonate, and lyophilized to give a solid. The solid was dissolved in water (5 ml) and this aqueous solution was subjected to column chromatography on Cephadex G-15 (trademark, made by Pharmacia Ficee Chemicals) (500 ml) and eluted with water. The fractions, containing the desired compound, were combined and lyophilized to give 2'-N-palmitoylkasugamycin (425 mg).

mp: 162° C. (dec.)
$[\alpha]_D^{26}$: +113.4° (C=0.58, $H_2O$)
IR (Nujol): 1660, 1540 $cm^{-1}$
NMR ($CD_3OD$, δ): 0.90 (3H, t, J=5 Hz), 1.20 (3H, d, J=5 Hz), 5.27 (1H, s)
FD Mass: 574 (M'-44)

EXAMPLE 2

Phosphorus oxychloride (0.66 ml) was added to a mixture of dimethylformamide (0.56 ml) and tetrahydrofuran (1 ml) at −5°–0° C.

The solution was stirred at 0°–5° C. for 5 minutes and cooled at −20°–−10° C. to give a suspension. To the suspension were added successively tetrahydrofuran (10 ml) and n-icosanoic acid (1.5 g) at −5°–0° C. with stirring. The mixture was stirred at the same temperature for 30 minutes to prepare an activated acid solution. To a solution of kasugamycin monohydrochloride (1 g) in a mixture of tetrahydrofuran (20 ml) and water (13 ml) was dropwise added the activated acid solution obtained above, keeping the pH 9.5-10.0 with triethylamine under ice-cooling. The mixture was stirred at the same temperature for 30 minutes and then at ambient temperature for an hour. The reaction mixture was adjusted to pH 3 with Amberlite IRA-120 ($H^\oplus$ form; trademark, made by Rhom and Haas Co.) at ambient temperature. The resin was filtered off and washed with a mixture of tetrahydrofuran and water (2:1 V/V). The filtrate and washings were combined and the solution was adjusted to pH 8.5 with Amberlite IRA-400 ($OH^\ominus$ type, trademark, made by Rhom and Haas Co.) at the same temperature. The resin was filtered off and washed with a mixture of tetrahydrofuran and water (2:1 V/V). The filtrate and washings were combined and the solution was concentrated under reduced pressure to give precipitates. The precipitates were collected by filtration, washed with water and diethylether, and air-dried to give 2'-N-icosanoylkasugamycin (1.84 g).

mp: 128°–134° C.
IR (Nujol): 3300, 1735, 1650, 1540, 1210, 1110, 1010 $cm^{-1}$
NMR ($CD_3OD$, δ): 0.95 (3H, m)
FD Mass: 630 (M+-44)

EXAMPLE 3

To a solution of kasugamycin monohydrochloride (1 g) in a mixture of tetrahydrofuran (20 ml) and water (13 ml), was dropwise added cis-13-docosenoylchloride (1 g) under ice-cooling with stirring, keeping the pH between 9.5 and 10.0 with triethylamine. The mixture was stirred at the same temperature for an hour. The reaction mixture was adjusted to pH 2.5 with Amberlite IRA-120 ($H^\oplus$ form; trademark, made by Rhom and Haas Co.) at ambient temperature. The resin was filtered off and washed with a mixture of tetrahydrofuran and water (2:1 V/V). The filtrate and washings were combined and the solution was adjusted to pH 8 with Amberlite IRA-400 ($OH^\ominus$ type, trademark, made by Rhom and Haas Co.) at ambient temperature.

The resin was filtered off and washed with a mixture of tetrahydrofuran and methanol (1:1 V/V). The filtrate and washings were combined and the solution was concentrated under reduced pressure until the organic layer was removed. The aqueous layer was filtered off and the filtrate was lyophilized to give 2'-N-(cis-13-docosenoyl)kasugamycin (2.35 g).

mp: 140°–143° C. (dec.)
IR (Nujol): 3300, 2600, 2500, 1660–1650, 1540, 1110, 1035 $cm^{-1}$
NMR ($CD_3OD$, δ): 0.96 (3H, m)

EXAMPLE 4

The following compounds were obtained according to similar manners to those of Examples 1, 2 and 3.

(1) 2'-N-Decanoylkasugamycin mp: 112°–115° C.
$[\alpha]_D^{18}$: +97.0° (C=1.0, $H_2O$)
IR (Nujol): 1660 $cm^{-1}$
NMR ($CDCl_3$, δ): 5.24 (1H, br s)
FD Mass: 490 (M+-43)

(2) 2'-N-Lauroylkasugamycin mp: 125°–130° C.
$[\alpha]_D^{18}$: +87.2° (C=1.0, $H_2O$)
IR (Nujol): 1650 $cm^{-1}$
NMR ($CDCl_3$, δ): 5.30 (1H, br s)
FD Mass: 518 (M+-43)

(3) 2'-N-Myristoylkasugamycin mp: 146°–147° C.
$[\alpha]_D^{20}$: +81.86° (C=0.489, MeOH)
IR (Nujol): 1650, 1540 $cm^{-1}$
NMR ($CD_3OD$, δ): 5.33 (1H, brs)
FD Mass: 546 (M+-44)

(4) 2'-N-Pentadecanoylkasugamycin mp: 144°–145° C.
$[\alpha]_D^{20}$: +73.92° (C=0.467, MeOH)
IR (Nujol): 1650, 1540 $cm^{-1}$
NMR ($CD_3OD$, δ): 5.27 (1H, brs)
FD Mass: 561 (M+-43)

(5) 2'-N-Stearoylkasugamycin mp: 152°–156° C.
$[\alpha]_D^{20}$: +76.23° (C=0.515, MeOH)
IR (Nujol): 1650, 1540 $cm^{-1}$
NMR ($CD_3OD$, δ): 5.27 (1H, brs)
FD Mass: 624 (M+-22), 596 (M+-50), 569 (M+-77)

(6) 2'-N-Docosanoylkasugamycin mp: 149°–155° C.
IR (Nujol): 3300, 2600, 2500, 1660, 1540, 1170, 1120, 1035 $cm^{-1}$

EXAMPLE 5

A solution of 2'-N-(cis-13-docosenoyl)kasugamycin (1 g) in a mixture of tetrahydrofuran (15 ml), water (15 ml), and 1N-hydrochloric acid (0.5 ml) was hydrogenated with hydrogen atmosphere at ambient temperature for 4 hours in the presence of 10% palladium on carbon (1 g). The catalyst was filtered off and the filtrate was concentrated under reduced pressure to give a residue. The residue was suspended with water (40 ml) and the suspension was lyophilized to give 2'-N-docosanoylkasugamycin (852 mg).

mp: 149°–155° C.

IR (Nujol): 3300, 2600, 2500, 1660, 1540, 1170, 1120, 1035 cm$^{-1}$

NMR (CD$_3$OD,δ): 0.95 (3H, m)

Having now fully described the invention, it will be apparent to one of ordinary skill in the art that many changes and modifications can be made thereto, without departing from the spirit or scope of the invention as set forth therein.

What is claimed as new and desired to be secured by Letters Patent in the United States is:

1. Aminoglycoside derivatives of the formula:

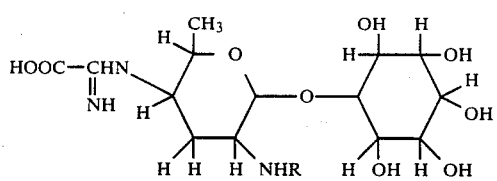

wherein R is higher alkanoyl or higher alkenoyl having 7 to 24 C atoms, and pharmaceutically acceptable salts thereof.

2. The compound of claim 1, wherein R is decanoyl, lauroyl, myristoyl, pentadecanoyl, palmitoyl, stearoyl, icosanoyl, docosanoyl or docosenoyl.

3. The compound of claim 2, which is 2'-N-palmitoylkasugamycin.

4. An anti-viral composition comprising as an active ingredient an effective amount of the compound of claim 1, and a pharmaceutically acceptable carrier or excipient.

5. A method of treating a viral infection comprising administering to a patient subjected to such infection an effective amount of the compound of claim 1 or pharmaceutically acceptable salts thereof.

6. The compound of claim 1, wherein R is further substituted with hydroxyl, amine or halogen.

7. The compound of claim 6, wherein the halogen substituent of R is chlorine, bromine, fluorine or iodine.

8. The compound of claim 1, wherein R is a higher alkanoyl which is further substituted with at least one hydroxyl, amine or halogen.

9. The compound of claim 1, wherein R is a higher alkenoyl which is further substituted with at least one hydroxyl, amine or halogen.

10. The compound of claim 1, wherein R is selected from the group consisting of octanoyl, decanoyl, lauroyl, myristoyl, pentadecanoyl, palmitoyl, heptadecanoyl, stearoyl, icosanoyl, docosanoyl, octenoyl, decenoyl, icosenoyl, and docosenoyl.

11. The compound of claim 1 in the form of an organic or inorganic salt selected from the group consisting of hydrochloride, hydrobromide, hydroiodide, sulfate, nitrate, carbonate, phosphate, acetate, fumarate, maleate, tartrate, methanesulfonate, benzenesulfonate, and toluenesulfonate.

12. The anti-viral composition of claim 4 in unit dosage form.

13. The method of claim 5, wherein the daily dosage of the anti-viral compound is 0.1 to 100 mg/kg of the patient.

* * * * *